(12) United States Patent
Meyer et al.

(10) Patent No.: US 9,527,782 B2
(45) Date of Patent: Dec. 27, 2016

(54) METHOD OF PREPARING A MODIFIED SUPPORT, A CATALYST PRECURSOR AND A CATALYST, AND A HYDROCARBON SYNTHESIS PROCESS USING THE CATALYST

(71) Applicant: SASOL TECHNOLOGY (PROPRIETARY) LIMITED, Rosebank (ZA)

(72) Inventors: Rita Meyer, Vereeniging (ZA); Jacobus Lucas Visagie, Sasolburg (ZA)

(73) Assignee: SASOL TECHNOLOGY (PROPIETARY) LIMITED (ZA)

( * ) Notice: Subject to any disclaimer, the term of this patent is extended or adjusted under 35 U.S.C. 154(b) by 0 days.

(21) Appl. No.: 14/408,726

(22) PCT Filed: Jul. 26, 2013

(86) PCT No.: PCT/IB2013/056139
§ 371 (c)(1),
(2) Date: Dec. 17, 2014

(87) PCT Pub. No.: WO2014/020507
PCT Pub. Date: Feb. 6, 2014

(65) Prior Publication Data
US 2015/0197461 A1 Jul. 16, 2015

(30) Foreign Application Priority Data

Aug. 2, 2012 (ZA) .................................. 2012/05837

(51) Int. Cl.
| | | |
|---|---|---|
| C07C 1/04 | (2006.01) |
| B01J 20/284 | (2006.01) |
| B01J 23/75 | (2006.01) |
| B01J 23/89 | (2006.01) |
| B01J 20/30 | (2006.01) |
| B01J 37/03 | (2006.01) |
| B01J 37/08 | (2006.01) |
| B01J 21/04 | (2006.01) |
| B01J 21/06 | (2006.01) |
| B01J 35/00 | (2006.01) |
| C10G 2/00 | (2006.01) |

(52) U.S. Cl.
CPC .............. *C07C 1/043* (2013.01); *B01J 20/284* (2013.01); *B01J 20/30* (2013.01); *B01J 21/04* (2013.01);
(Continued)

(58) Field of Classification Search
CPC ........... B01J 21/04; B01J 21/063; B01J 23/75; B01J 36/0006; B01J 35/002; B01J 37/033; B01J 37/08; B01J 23/8913; B01J 20/284; B01J 20/30; C07C 1/043; C07C 1/0445; C10G 2/33
See application file for complete search history.

(56) References Cited

U.S. PATENT DOCUMENTS

| | | |
|---|---|---|
| 4,595,703 A | 6/1986 | Payne et al. |
| 6,100,304 A | 8/2000 | Singleton et al. |

(Continued)

FOREIGN PATENT DOCUMENTS

| | | |
|---|---|---|
| EP | 1736239 A1 | 12/2006 |
| EP | 1187674 B1 | 10/2008 |

(Continued)

*Primary Examiner* — Jafar Parsa
*Assistant Examiner* — Medhanit Bahta
(74) *Attorney, Agent, or Firm* — Fellers, Snider, Blankenship, Bailey & Tippens, P.C.

(57) ABSTRACT

A method of preparing a modified catalyst support comprises preparing a titanium-containing catalyst support material by (i) contacting a catalyst support material with an organic titanium compound, or (ii) co-hydrolyzing a hydrolysable organic titanium compound and Al(OR")3, with the titanium-containing catalyst support material then including Al, wherein all R" are the same or different and are each an (Continued)

organic group. The titanium-containing catalyst support material is calcined at a temperature above 900° C. to obtain a modified catalyst support which includes more than 1 wt % and less than 3.5 wt % Ti, based on the mass of the catalyst support material in the modified catalyst support, the Ti being present in the form of one or more titanium compounds.

13 Claims, 3 Drawing Sheets

(52) U.S. Cl.
CPC ............... *B01J 21/063* (2013.01); *B01J 23/75* (2013.01); *B01J 23/8913* (2013.01); *B01J 35/002* (2013.01); *B01J 35/0006* (2013.01); *B01J 37/033* (2013.01); *B01J 37/08* (2013.01); *C07C 1/0445* (2013.01); *C10G 2/33* (2013.01)

(56) References Cited

U.S. PATENT DOCUMENTS

| | | | |
|---|---|---|---|
| 6,191,066 B1 * | 2/2001 | Singleton | B01J 23/75 502/303 |
| 6,255,358 B1 | 7/2001 | Singleton et al. | |
| 6,875,720 B2 * | 4/2005 | Van Berge | B01J 21/12 502/103 |
| 7,365,040 B2 | 4/2008 | Van Berge et al. | |
| 2003/0017943 A1 | 1/2003 | Shan et al. | |
| 2003/0143421 A1 | 7/2003 | Price et al. | |
| 2005/0272827 A1 | 12/2005 | Lok | |
| 2006/0246000 A1 | 11/2006 | Dolling et al. | |
| 2010/0022670 A1 | 1/2010 | Soled et al. | |
| 2012/0122671 A1 * | 5/2012 | Polli | B01J 21/12 502/263 |

FOREIGN PATENT DOCUMENTS

| | | |
|---|---|---|
| WO | 99/42214 | 8/1999 |
| WO | 9961550 | 12/1999 |
| WO | 00/20116 | 4/2000 |
| WO | 0071253 A2 | 11/2000 |
| WO | 02/07883 A2 | 1/2002 |
| WO | 03/012008 A2 | 2/2003 |
| WO | 2004028687 A1 | 4/2004 |
| WO | 2004035511 A2 | 4/2004 |
| WO | 2008104793 A2 | 9/2008 |
| WO | 2011043995 A1 | 4/2011 |
| WO | 2012/044591 A2 | 4/2012 |
| WO | 2012107844 A1 | 8/2012 |
| WO | 2013123315 A1 | 8/2013 |
| WO | WO2013123166 A1 | 8/2013 |
| WO | PCT/IB2013/056139 | 1/2014 |

* cited by examiner

METHOD OF PREPARING A MODIFIED SUPPORT, A CATALYST PRECURSOR AND A CATALYST, AND A HYDROCARBON SYNTHESIS PROCESS USING THE CATALYST

FIELD OF THE INVENTION

THIS INVENTION relates to catalysts. More particularly, it relates to a method of preparing a modified catalyst support, to a method of preparing a catalyst precursor, to a method of preparing a catalyst, and to a hydrocarbon synthesis process employing the catalyst.

BACKGROUND ART

Hydrocarbon synthesis from hydrogen and carbon monoxide in the presence of a Fischer-Tropsch catalyst is commonly known as Fischer-Tropsch (FT) synthesis. FT synthesis forms part of gas-to-liquids, coal-to-liquids, and biomass-to-liquids processes in which natural gas, coal, and biomass respectively are usually converted by means of a three step process into liquid hydrocarbons. The three process steps are normally (i) production of synthesis gas (or 'syngas') comprising a mixture of hydrogen and carbon monoxide from natural gas, coal, or biomass respectively, (ii) conversion of the syngas into hydrocarbons or syncrude by means of FT synthesis, and (iii) a hydrocracking or hydrotreating step to convert the syncrude into products such as liquid transportation fuels including diesel, petrol, jet fuel, as well as naphtha.

During the FT synthesis described in step (ii) above the syngas in the form of CO and $H_2$ is contacted with a FT synthesis catalyst under FT synthesis conditions to produce the hydrocarbons. One type of catalyst which is often used in low temperature FT (LTFT) synthesis comprises an active catalyst component such as Co on a catalyst support such as alumina, silica, titania, magnesia or the like, and the hydrocarbons produced are usually in the form of a waxy hydrocarbon product.

Contamination of the hydrocarbon product produced during FT synthesis with ultra fine particulate matter derived from the support such as alumina, and the active catalyst component such as Co, is experienced. This results in loss of the expensive active catalyst component as well as fouling of the downstream processes described in (iii) above with the support and active catalyst component ultra fine particles. It is believed that this hydrocarbon product contamination is as a result of one or both of: (a) Catalyst support dissolution during aqueous impregnation of the catalyst support with the active catalyst component (during preparation of the catalyst) which may result in precipitation and coating of the bulk support material with a physically bonded amorphous layer of the support material whereon the active catalyst component is deposited—this amorphous layer is insufficiently anchored and results in dislodgement of and washing out of active catalyst component rich ultra fine particles during FT synthesis; and (b) The FT synthesis catalyst is susceptible to hydrothermal attack that is inherent to realistic FT synthesis conditions. Such a hydrothermal attack on exposed and unprotected support material will result in contamination of the hydrocarbon product with ultra fine particular matter rich in the active catalyst component.

WO 99/42214, WO 02/07883, WO 03/012008 and U.S. Pat. No. 7,365,040 all disclose modification of a FT synthesis catalyst support with a modifying component to reduce the dissolution of the catalyst support in aqueous environment, including hydrothermal attack thereby to reduce the negative effect of ultra fine particles rich in active catalyst component contaminating the hydrocarbon product. These documents focus on Si as a modifying component, but a large number of other modifying components such as Zr, Ti, Cu, Zn, Mn, Ba, Co, Ni, Na, K, Ca, Sn, Cr, Fe, Li, Tl, Mg, Sr, Ga, Sb, V, Hf, Th, Ce, Ge, U, Nb, Ta, W and La are also mentioned.

It has now surprisingly been found that when a catalyst support is modified with low levels of titanium instead of silicon, solubility of the support is even further reduced. Even more surprisingly it has also been found that when the titanium containing support is calcined at a temperature above 900° C., the solubility of a FT synthesis catalyst or support prepared from the titanium modified support can be further reduced to even more acceptable levels. It was also unexpectedly found that, in at least some cases, the C5+ selectivity of the catalyst prepared from the titanium modified support in FT synthesis improved compared to a catalyst made from an unmodified support.

When a catalyst support is modified with Si, calcination of the silica containing support prior to impregnation with an active metal component, such as Co, takes place at a temperature of about 500° C. (see WO 99/42214 on page 15 line 9). This temperature is well below the calcination temperature set by the invention, i.e. greater than 900° C. The inventors have found that when a silica modified support is calcined at temperatures higher than the normal calcination temperature of about 500° C. for calcining such modified supports, the solubility of the modified support calcined at the higher temperatures is higher than the solubility at about 500° C. It was accordingly most surprisingly found that when titanium is used as a modifying component and the titanium containing support is then calcined at the higher temperatures described above, the solubility of the titanium modified catalyst support is reduced compared to the titanium modified catalyst support calcined at lower temperatures.

Most surprisingly, it was also found that the titanium has to be present on the catalyst support at a low level range, otherwise the mechanical strength of the support decreases, indicating a lower attrition resistance of the support. Lower attrition resistance of the support will result in breaking-up of the support during FT synthesis leading to loss of catalyst. The importance of the low level range for the titanium was not realised in the prior art such as WO 2012/044591.

DISCLOSURE OF THE INVENTION

According to a first aspect of the invention, there is provided a method of preparing a modified catalyst support, the method comprising preparing a titanium-containing catalyst support material by
  (i) contacting a catalyst support material with an organic titanium compound, or
  (ii) co-hydrolysing a hydrolysable organic titanium compound and Al(OR")$_3$, with the titanium-containing catalyst support material then including Al,
    wherein all R" are the same or different and are each an organic group; and calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds.

According to a second aspect of the invention, there is provided a method of preparing a catalyst precursor, the method comprising preparing a titanium-containing catalyst support material by
  (i) contacting a catalyst support material with an organic titanium compound, or
  (ii) co-hydrolysing a hydrolysable organic titanium compound and Al(OR")$_3$, with the titanium-containing catalyst support material then including Al,
    wherein all R" are the same or different and are each an organic group;
  calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds; and
  introducing a precursor compound of an active catalyst component onto and/or into the modified catalyst support thereby to obtain a catalyst precursor.

Thus, in the methods of the invention, sufficient of the organic titanium compound or hydrolysable organic titanium compound is used initially, i.e. to prepare the titanium-containing catalyst support material, so that, when the titanium-containing support material is calcined at the temperature above 900° C., the modified catalyst support that is thereby obtained includes titanium, in the form of the one or more titanium compounds, in an amount more than 1 wt % and less than 3.5 wt % titanium, based on the weight of the modified catalyst support.

Preparing the Titanium-Containing Support Material
Contacting of the Catalyst Support Material with the Organic Titanium Compound By contacting the catalyst support material with the organic titanium compound, the organic titanium compound may be introduced onto and/or into the catalyst support material.

In a preferred embodiment of the invention, the catalyst support material is at least partially soluble in an aqueous acid solution and/or in a neutral aqueous solution.

The catalyst support material may be selected from the group consisting of a catalyst support precursor which is convertible to a catalyst support upon calcination thereof; and a catalyst support.

When the catalyst support material is the catalyst support precursor, it may be a compound which, upon calcination, converts to a catalyst support in the form of an oxide, preferably a metal oxide. Preferably, the metal oxide is an oxide of a metal selected from the group consisting of Al, Si, Mg and Zn. More particularly, the catalyst support precursor may then comprise an aluminium compound which converts to one or more aluminium oxides upon calcination. Preferably, the aluminium compound is Al(OH)$_3$ (such as, for example, gibbsite and/or bayerite) and/or AlO(OH), and more preferably it is boehmite. The catalyst support precursor may be shaped into particulate form after the introduction of the titanium compound onto and/or into the catalyst support precursor and before calcination thereof. The shaping may, for example, be carried out by means of spray drying. Prior to shaping the catalyst support precursor, it may be partially dried. The resulting shaped product is then subjected to the calcination above 900° C. The calcination takes place prior to introducing the precursor compound of the active catalyst component onto and/or into the shaped product. In order to achieve a desired particle size distribution, classification may be performed on the shaped particulate product, using, for example, cyclones or sieves.

However, the catalyst support material is preferably a catalyst support. The catalyst support may then be any catalyst support suitable for supporting thereon the active catalyst component or a precursor compound of the active catalyst component. The catalyst support is preferably suitable for use as a support in a catalyst for synthesising hydrocarbons and/or oxygenates of hydrocarbons from at least hydrogen and carbon monoxide, particularly a Fischer-Tropsch (FT) synthesis catalyst. The FT synthesis catalyst may be for use in a process to be performed in a fixed bed reactor, slurry bed reactor or even a fixed fluidized bed reactor. Preferably, the process is to be performed in a three phase slurry bed FT synthesis reactor.

The catalyst support is usually a porous support, and preferably it is also pre-shaped. The porous support preferably has an average pore diameter from 8 to 50 nanometers, more preferably from 10 to 15 nanometers. The pre-shaped support may be a particulate support, preferably with an average particle size of from 1 to 500 micrometers, more preferably from 10 to 250 micrometers, and still more particularly from 45 to 200 micrometers.

The catalyst support may be selected from the group consisting of alumina in the form of one or more aluminium oxides; silica (SiO$_2$); magnesia (MgO); zinc oxide (ZnO); silica-alumina and mixtures thereof. Preferably, the support is selected from the group consisting of alumina in the form of one or more aluminium oxides; and silica (SiO$_2$). More preferably, the support is alumina in the form of one or more aluminium oxides.

The one or more aluminium oxides may be selected from the group including (preferably consisting of) gamma alumina, delta alumina, theta alumina and a mixture of two or more thereof. Some alpha alumina may form after calcination of the titanium-containing catalyst support. Preferably the group includes, or, more preferably, consists of, gamma alumina, delta alumina and a mixture of gamma alumina and delta alumina. The aluminium oxide catalyst support may be that obtainable under the trademark Puralox, preferably Puralox SCCa 150, from SASOL Germany GmbH. Puralox SCCa 150 is a spray-dried aluminium oxide support consisting of a mixture of gamma and delta aluminium oxide.

The aluminium oxide may be a crystalline compound which can be represented by the formula Al$_2$O$_3$.xH$_2$O where 0<x<1. The term 'aluminium oxide' thus excludes Al(OH)$_3$, and AlO(OH), but includes compounds such as gamma, delta and theta alumina.

As set out above, the catalyst support material is contacted with an organic titanium compound. In this specification, an organic titanium compound is a titanium compound wherein titanium is associated with at least one organic group by means of a bond, for instance by means of a covalent bond, a metal-to-ligand coordination or an ionic interaction. Preferably, in the organic titanium compound, titanium is associated with at least one non-carbon atom of the at least one organic group, in particular with an oxygen atom of the organic group. In one embodiment of the invention, at least one organic group of the organic titanium compound may be a chelating compound, preferably a chelating compound which binds to titanium by means of at least one non-carbon atom, preferably an oxygen atom (preferably by means of two oxygen atoms). Preferably, all the groups associated with the titanium are organic groups, and preferably all the said organic groups are associated with the titanium via an oxygen atom.

In one embodiment of the invention some, but preferably all, the organic groups are of the formula —(O)—R where R is an organic group. R in different —(O)—R groups may be the same or different. R of an —(O)—R group may be bound, or may not be bound, to R of another —(O)—R group. R may be an acyl or hydrocarbyl group or it may be a heterohydrocarbyl group (that is, an organic group consisting of carbon, hydrogen and at least one atom which is not carbon or hydrogen), preferably a hydrocarbyl group, preferably an alkyl group, and preferably an alkyl group with not more than eight carbon atoms. Alternatively, R may be of the formula —$OR^1$ where $R^1$ may be a hydrocarbyl group or it may be a heterohydrocarbyl group (that is, an organic group consisting of carbon, hydrogen and at least one atom which is not carbon or hydrogen), preferably an alkyl group, preferably an alkyl group and preferably an alkyl group with not more than eight carbon atoms.

In one embodiment of the invention, the organic titanium compound may be selected from the group consisting of titanium (IV) methoxide; titanium (IV) ethoxide; titanium (IV) propoxide; titanium (IV) isopropoxide; titanium (IV) diisopropoxide bis(acetylacetonate); titanium (IV) 2-ethylhexoxide; titanium (IV) hexoxide; titanium(IV) butoxide and titanium (IV) bis(ammonium lactato)dihydroxide.

The contacting of the catalyst support material with the titanium compound may be by any suitable method including, for example, impregnation, precipitation or chemical vapour phase deposition. Preferably, the contacting of the titanium compound with the catalyst support material is by means of impregnation. A suitable impregnating liquid medium may be used to effect the contact between the titanium compound and the catalyst support material. The impregnation may be incipient wetness impregnation, but preferably it is slurry phase impregnation. Preferably, the liquid medium is a non-aqueous medium, such as an organic liquid medium, and preferably it an alcohol such as ethanol. Alternatively, the liquid medium is an inorganic liquid medium, such as water. Preferably, the liquid medium is a solvent for the titanium compound.

The impregnation is preferably carried out at a temperature above 25° C. The temperature may be 50-60° C. The impregnation may be carried out for a period of from 1 minute to 20 hours, preferably from 1 minute to 5 hours. The impregnation may be effected at atmospheric pressure.

After impregnation, the excess impregnation liquid medium may be removed, preferably by means of drying. The drying is preferably carried out at sub-atmospheric conditions, preferably from 0.01 to 0.1 bar(a). The drying is preferably carried out at temperature above 25° C., more preferably at a temperature of not more than 125° C.

It will be appreciated that the catalyst support material can be contacted, if desired, with another metallic compound to enhance the reduction in support solubility. However, should such another metallic compound be used, it is preferably not a tungsten compound.

Co-Hydrolysing the Hydrolysable Titanium Compound and Al(OR")$_3$

Co-hydrolysis of the hydrolysable organic titanium compound and Al(OR")$_3$ may be carried out by mixing the hydrolysable organic titanium compound and Al(OR")$_3$ and hydrolysing the mixture. Hydrolysis of the mixture may be carried out by adding water to the mixture.

Preferably, the titanium-containing catalyst support material which includes Al, which is formed by the co-hydrolysis, is titanium-containing boehmite. The co-hydrolysis process may also include the step of separating the titanium-containing boehmite from other products that form during the co-hydrolysis. The titanium-containing boehmite may be dried, and preferably it is shaped into particulate form before calcination thereof. The shaping may be carried out by means of spray drying. The resulting shaped product is then subjected to the calcination above 900° C. The calcination takes place prior to introducing the precursor compound of the active catalyst component onto and/or into the shaped product. In order to achieve a desired particle size distribution, classification may be performed on the shaped particulate product, using, for example, cyclones or sieves.

In this specification, a hydrolysable organic titanium compound is a titanium compound wherein titanium is associated with at least one oxygen atom of at least one organic group by means of a bond, for instance by means of a covalent bond, a metal to ligand coordination or an ionic interaction. In one embodiment of the invention, at least one organic group of the hydrolysable organic titanium compound may be a chelating compound, preferably a chelating compound which binds to titanium by means of at least one oxygen atom (preferably two oxygen atoms). Preferably, all the groups associated with the titanium are organic groups, and preferably all the said organic groups are associated with the titanium via an oxygen atom.

In one embodiment of the invention the hydrolysable organic titanium compound may be Ti(OR')4 wherein all R' are the same or different and each are an organic group. R' of an —(OR') group may be bound, or may not be bound, to R' of another —(OR') group. R' may be an acyl or hydrocarbyl group or it may be a heterohydrocarbyl group (that is, an organic group consisting of carbon, hydrogen and at least one atom which is not carbon or hydrogen), preferably a hydrocarbyl group, preferably an alkyl group, and preferably an alkyl group with not more than twelve carbon atoms, preferably an alkyl group with not more than eight carbon atoms. Preferably, R' is an alkyl with more than two carbon atoms. In one preferred embodiment of the invention R' is hexyl. Preferably, all the R' groups are the same.

In one embodiment of the invention, the hydrolysable organic titanium compound may be selected from the group consisting of titanium (IV) methoxide; titanium (IV) ethoxide; titanium (IV) propoxide; titanium (IV) isopropoxide; titanium (IV) diisopropoxide bis(acetylacetonate); titanium (IV) 2-ethylhexoxide; titanium (IV) hexoxide; titanium(IV) butoxide and titanium (IV) bis(ammonium lactato)dihydroxide.

R" of an (OR") group may be bound, or may not be bound, to R" of another (OR") group. R" may be an acyl or hydrocarbyl group or it may be a heterohydrocarbyl group (that is, an organic group consisting of carbon, hydrogen and at least one atom which is not carbon or hydrogen), preferably a hydrocarbyl group, preferably an alkyl group, and preferably an alkyl group with not more than twelve carbon atoms. Preferably, R" is an alkyl with more than two carbon atoms. In one preferred embodiment of the invention R" is hexyl. Preferably, all the R" groups are the same.

Calcination of the Titanium-Containing Support Material

The calcination of the titanium-containing catalyst support material may take place in a non-reducing environment, preferably in an oxidizing environment, such as in air. The calcination may be carried out either in a stationary or in a fluidized bed calciner. The calcination may instead take place in a rotary kiln. Most preferred, however, is a rotary kiln. The calcination may typically take place for a period of 10 min to 10 hours. More preferably, the calcination may be effected for a period of about 20 min to 2.5 hours.

During the calcination of the titanium-containing catalyst support material prepared by contacting the catalyst support material with the organic titanium compound, the organic titanium compound in and/or on the catalyst support material may react and/or it may decompose and/or it may bond chemically to the catalyst support material; however, preferably, the calcination transforms the organic titanium compound to a titanium oxide, preferably by decomposition and/or reaction. During calcination of the titanium-containing catalyst support material prepared by co-hydrolysis, conversion to aluminium-titanium oxide may take place.

The calcination of the titanium-containing support material is preferably carried out at or above 910° C., preferably at at least 960° C., more preferably at above 990° C., still more preferably at at least 1000° C. The calcination temperature may be at or above 1050° C. in some cases. Preferably the calcination is carried out below 1200° C., preferably below 1150° C.

Ti Level after Calcination

After calcination, titanium, in the form of the one or more titanium compounds, may be present in and/or on the catalyst support material in an amount of more than 1.5 wt %, preferably at least 2.0 wt %, more preferably at least 2.5 wt % Ti, based on the weight of the modified catalyst support. After calcination, titanium, in the form of the one or more titanium compounds, may be present in and on the catalyst support material in an amount of less than 3.5 wt %, preferably not more than 3 wt %, preferably less than 3 wt % Ti, based on the weight of the modified catalyst support. The preferred amount of titanium, in the form of the one or more titanium compounds, present in and on the catalyst support material after calcination is about 2.6 wt % Ti based on the weight of the modified catalyst support.

Introducing the Precursor Compound of the Active Catalyst Component, onto and/or into the Modified Catalyst Support The active catalyst component may be a known component active for hydrocarbon synthesis process (preferably a FT synthesis process), and may be selected from the group consisting of cobalt (Co), iron (Fe), nickel (Ni) and ruthenium (Ru). Cobalt (Co) is preferred.

The precursor compound of the active catalyst component may thus be any suitable compound of the active catalyst component. Preferably, it is an inorganic compound, more preferably an inorganic salt of the active catalyst component. The precursor compound of the active catalyst component may be cobalt nitrate, and particularly it may be $Co(NO_3)_2 \cdot 6H_2O$.

The precursor compound of the active catalyst component may be introduced onto and/or into the modified catalyst support by any suitable manner, but preferably it is by means of impregnation. Preferably, the modified catalyst support is impregnated with the precursor compound of the active catalyst component by forming a mixture of the said precursor compound; a liquid carrier for the said precursor compound; and the modified catalyst support.

The liquid carrier may comprise a solvent for the precursor compound of the active catalyst component and preferably the said precursor compound is dissolved in the liquid carrier. The liquid carrier may be water.

The impregnation may be effected by any suitable impregnation method, including incipient wetness impregnation or slurry phase impregnation. Slurry phase impregnation is preferred. Preferably, the precursor compound of the active catalyst component is dissolved in the liquid carrier in order that the volume of the solution is greater than xy liter, which solution is then mixed with the modified catalyst support, and wherein x is the BET pore volume of the modified catalyst support in l/kg support, and y is the mass of modified catalyst support to be impregnated in kg. Preferably the volume of the solution is greater than 1.5xy liter ("l"), and preferably it is about 2xy liter.

The impregnation may be carried out at sub-atmospheric pressure, preferably below 85 kPa(a), preferably at 20 kPa(a) and lower. Preferably the impregnation is also carried out at a temperature above 25° C. The impregnation temperature may be above 40° C., preferably above 60° C., but preferably not above 95° C.

The impregnation may be followed by partial drying of the impregnated support, preferably at a temperature above 25° C. The drying temperature may be above 40° C., preferably above 60° C., but preferably not above 95° C. Preferably the partial drying may be effected at sub-atmospheric conditions, preferably below 85 kPa(a), preferably at 20 kPa(a) or lower.

In one embodiment of the invention, the impregnation and partial drying of the modified catalyst support may be carried out using a procedure which includes a first step wherein the modified catalyst support is impregnated (preferably slurry impregnated) with the precursor compound of the active catalyst component at a temperature above 25° C., and at sub-atmospheric pressure, and the resultant product is dried; and at least one subsequent step wherein the resulting partially dried impregnated modified catalyst support of the first step is subjected to treatment at a temperature above 25° C., and sub-atmospheric pressure such that the temperature of the subsequent step exceeds that in the first step and/or the sub-atmospheric pressure in the subsequent step is lower than that in the first step. This two step impregnation procedure may be as described in WO 00/20116, which is incorporated herein by reference.

A dopant capable of enhancing the reducibility of the catalyst component of the active catalyst component may also be introduced onto and/or into the modified catalyst support. The dopant may be introduced during or after the introduction of the precursor compound of the active catalyst component onto and/or into the modified catalyst support. The dopant may be introduced as a dopant compound which is a compound of a metal selected from the group including palladium (Pd), platinum (Pt), ruthenium (Ru), rhenium (Re) and a mixture of two or more thereof. Preferably, the dopant compound is an inorganic salt, and it is preferably soluble in water. The mass proportion of the metal of the dopant to the active catalyst component metal may be in the ratio of 0.01:100 to 3:100.

The partially dried catalyst support with the precursor compound of the active catalyst component thereon and/or therein may be calcined. The calcination may be effected in order to decompose the catalyst precursor compound and/or to cause it to react with oxygen. During calcination an oxide or oxides of the active catalyst component may be formed. For example, a cobalt compound such as cobalt nitrate may be converted into a compound selected from CoO, CoO(OH), $Co_3O_4$, $Co_2O_3$ or a mixture of two or more thereof.

The calcination may be carried out in any suitable manner such as in a rotary kiln, but preferably it is carried out in a fluidised bed reactor.

The calcination may be carried out in an inert atmosphere, but preferably it is carried out in an oxidizing atmosphere, preferably in the presence of oxygen, more preferably in air.

Preferably the calcination is carried out at a temperature above 95° C., more preferably above 120° C., still more preferably above 200° C., but preferably not above 400° C., more preferably not above 300° C. This is especially the case where Co is the active catalyst component.

The calcination may be carried out by using a heating rate and an air space velocity that comply with the following criteria:
(i) when the heating rate is ≤1° C./min, the air space velocity is at least 0.76 m$_n^3$/(kg Co(NO$_3$)$_2$.6H$_2$O)/h; and
(ii) when the heating rate is higher than 1° C./min, the air space velocity satisfies the relation:

$$\log(\text{space velocity}) \geq \log 0.76 + \frac{\log 20 - \log 0.76}{2} \log(\text{heating rate})$$

The above conditions for air space velocity and heating rate are especially applicable where Co is the active catalyst component.

The impregnation, the partial drying and calcination may be repeated to achieve higher loadings of the precursor compound of the active catalyst component on the catalyst support. In one embodiment of the invention, a first impregnation, drying and calcination procedure may be followed by a partial reduction procedure of the calcined material; and the partially reduced material may then be subjected to a further impregnation, drying and calcination procedure. The partial reduction procedure may be executed with a final temperature of between 100° C. and 300° C., especially in the case where Co is the active catalyst component.

In one embodiment of the invention, the catalyst precursor may be prepared by a method which includes in a first preparation step, impregnating the modified catalyst support with an organic metal compound of the active catalyst component in a carrier liquid, at least partially drying the impregnated support, and calcining the at least partially dried impregnated support, to obtain a calcined intermediate; and in a second preparation step, impregnating the calcined intermediate from the first impregnation step, with an inorganic metal salt of the active catalyst component in a carrier liquid, at least partially drying the impregnated support, and calcining the at least partially dried impregnated support, to obtain the catalyst precursor. The organic metal compound may be an organic cobalt compound.

The catalyst precursor may have reduced dissolution in an aqueous environment, preferably an acidic aqueous environment.

Activation

According to a third aspect of the invention, there is provided a method of preparing a catalyst, which includes
preparing a titanium-containing catalyst support material by
(i) contacting a catalyst support material with an organic titanium compound, or
(ii) co-hydrolysing a hydrolysable organic titanium compound and Al(OR")$_3$, with the titanium-containing catalyst support material then including Al, wherein all R" are the same or different and are each an organic group;
calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds;
introducing a precursor compound of an active catalyst component onto and/or into the modified catalyst support thereby to obtain a catalyst precursor, and
reducing the said catalyst precursor, thereby activating the catalyst precursor and obtaining the catalyst.

The preparation of the titanium-containing catalyst support material, the calcination thereof to obtain the modified catalyst support, and the introduction of the precursor compound of the active catalyst component onto and/or into the modified catalyst support are thus in accordance with the method of preparing the catalyst precursor of the second aspect of the invention.

The reduction of the catalyst precursor preferably includes treating it with a reducing gas to activate it. Preferably, the reducing gas is hydrogen or a hydrogen containing gas. The hydrogen containing gas may consist of hydrogen and one or more inert gases which are inert in respect of the active catalyst. The hydrogen containing gas preferably contains at least 90 volume % hydrogen.

The reducing gas may be contacted with the catalyst precursor in any suitable manner. Preferably the catalyst precursor is provided in the form of a bed with the reducing gas being caused to flow through the bed of particles. The bed of particles may be a fixed bed, but preferably it is a fluidised bed and preferably the reducing gas acts as the fluidising medium for the bed of catalyst precursor particles.

The reduction may be carried out at a pressure from 0.6 to 1.5 bar(a), preferably from 0.8 to 1.3 bar(a). Alternatively the pressure may be from 1.5 bar(a) to 20 bar(a). Preferably, however, the pressure is at about atmospheric pressure.

The reduction is preferably carried out at a temperature above 25° C. at which the catalyst precursor will be reduced to an active form. Preferably, the activation is carried out at a temperature above 150° C., and preferably below 600° C., especially where the active catalyst component is cobalt. Preferably the reduction is carried out at a temperature below 500° C., more preferably below 450° C.

During activation the temperature may be varied, and preferably it is increased to a maximum temperature as set out above.

The flow of the reducing gas through the catalyst bed is preferably controlled to ensure that contaminants produced during reduction are maintained at a sufficiently low level. The reducing gas may be recycled, and preferably the recycled reducing gas is treated to remove one or more contaminants produced during reduction. The contaminants may comprise one or more of water and ammonia.

The activation may be carried out in two or more steps during which one or both of the heating rate and the space velocity of the reducing gas is varied.

In one embodiment of the invention, the active catalyst may be coated by introducing a mixture of active catalyst particles and a coating medium in the form of molten organic substance, which is at a temperature T$_1$, and which sets or congeals at a lower temperature T$_2$ so that T$_2$<T$_1$, into at least one mould; and at least partly submerging the mould in a cooling liquid, so as to cool the organic substance down to a temperature T$_3$, where T$_3$≤T$_2$.

During the activation the water partial pressure is preferably kept as low as possible, more preferably below 0.1 atmosphere. The hydrogen space velocity may be from 2 to 4 liters per hour per gram of catalyst.

Hydrocarbon Synthesis

According to a fourth aspect of the present invention, there is provided a hydrocarbon synthesis process which comprises
preparing a titanium-containing catalyst support material by
(i) contacting a catalyst support material with an organic titanium compound, or (ii) co-hydrolysing a hydrolysable organic titanium compound and Al(OR")$_3$, with the titanium-containing catalyst support material then including Al, wherein all R" are the same or different and are each an organic group;

calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds;

introducing a precursor compound of an active catalyst component onto and/or into the modified catalyst support thereby to obtain a catalyst precursor;

reducing the said catalyst precursor, thereby activating the catalyst precursor and obtaining the catalyst; and contacting hydrogen with carbon monoxide at a temperature above 100° C. and a pressure of at least 10 bar with the catalyst, to produce hydrocarbons and, optionally, oxygenates of hydrocarbons.

The preparation of the titanium-containing catalyst support material, the calcination thereof to obtain the modified catalyst support, the introduction of the precursor compound of the active catalyst component onto and/or into the modified catalyst support, and the reduction of the catalyst precursor are thus in accordance with the method of preparing the catalyst of the third aspect of the invention.

The temperature may be from 180° C. to 250° C., more preferably from 210° C. to 240° C. The pressure more preferably may be from 10 bar to 70 bar.

Preferably, the hydrocarbon synthesis process is a Fischer-Tropsch process, more preferably a three phase Fischer-Tropsch process, still more preferably a slurry bed Fischer-Tropsch process for producing a wax product.

The hydrocarbon synthesis process may also include a hydroprocessing step for converting the hydrocarbons and, optionally, oxygenates to liquid fuels and/or chemicals.

The present invention extends also to products produced by the hydrocarbon synthesis process of the fourth aspect of the invention.

The invention will now be described in more detail with reference to the accompanying drawings and the following non-limiting examples.

EXAMPLES

Figure 1:
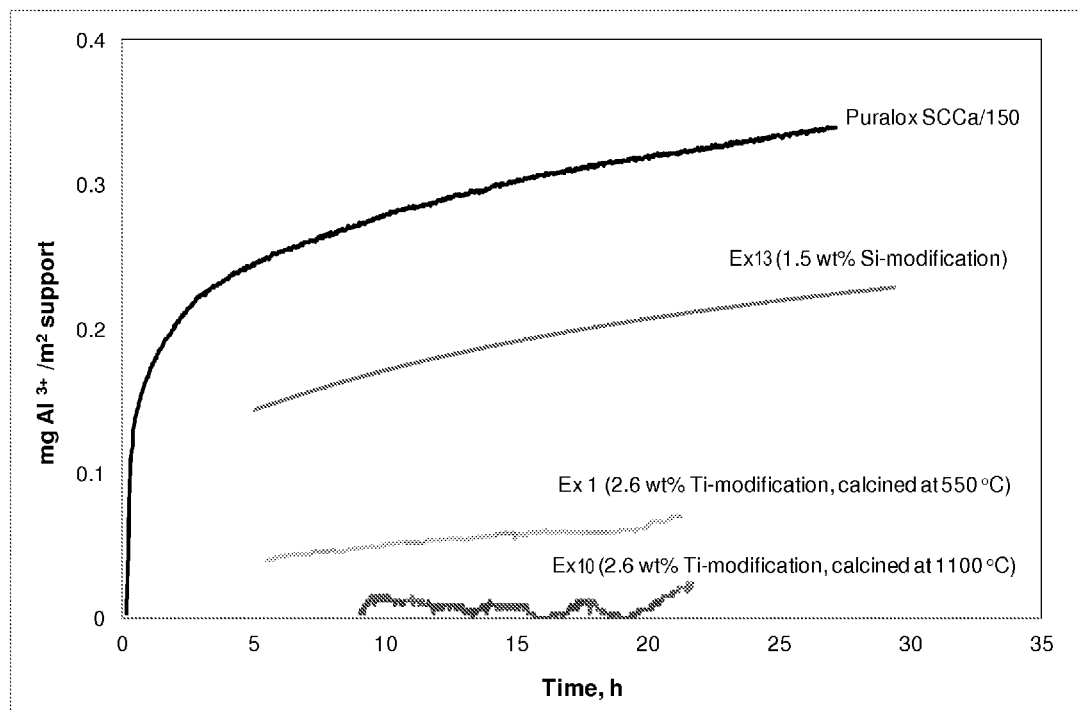
FIG. 1 shows cumulative Al dissolution as a function of time for a Ti-modified catalyst support (Example 1, Example 10), Si-modified catalyst support (Example 13) and unmodified alumina support (Puralox SCCa-/150)

In the Examples hereunder, expression of the titanium content of the catalyst supports in weight percentage ('wt %') is based on the weight of the modified catalyst supports. In Examples 1 to 12, 17 to 27, 29, 30, 32 and 36, during calcination of the titanium-containing catalyst support material, the organic titanium compound is transformed by decomposition and/or reaction into titanium oxide(s) so that the titanium, in the modified catalyst supports, is predominantly, or even wholly, in the form of the titanium oxide(s).

In Example 37, during calcination of the titanium-containing catalyst support material, conversion to aluminium-titanium oxide takes place.

Example 1

Comparative

Technical grade Ti(OC$_2$H$_5$)$_4$ was purchased from Sigma Aldrich and was used as is. Ti(OC$_2$H$_5$)$_4$ (14.65 g) was mixed with 85 ml ethanol and the mixture allowed to homogenize while stirring at 60 rpm and 60° C. 100 g of Puralox SCCa-150 catalyst support was added to the ethanol mixture and stirred for 10 minutes where after the solvent was removed under vacuum to obtain a titanium-containing catalyst support material in the form of a free flowing powder. The powder was kept in a vacuum oven at 120° C. overnight, followed by calcination at 550° C. from room temperature using a heating rate of 1° C./min, and hold for 2 hours at the final temperature of 550° C. in static air. The resulting modified catalyst support contained Ti (2.6 wt %) deposited onto the alumina, as determined by ICP (Inductive Coupled Plasma) analysis.

Example 2

Comparative

A modified catalyst support was prepared, as described in Example 1, however, the calcination temperature was 600° C.

Example 3

Comparative

A modified catalyst support was prepared, as described in Example 1, however, the calcination temperature was 700° C.

Example 4

Comparative

A modified catalyst support was prepared, as described in Example 1, however, the calcination temperature was 800° C.

Example 5

Inventive

A modified catalyst support was prepared, as described in Example 1, however, the calcination temperature was 910° C.

Example 6

Inventive

A modified catalyst support was prepared, as described in Example 1, however, the calcination temperature was 960° C.

Example 7

Inventive

A modified catalyst support was prepared, as described in Example 1, however, the calcination temperature was 990° C.

Example 8

Inventive

A modified catalyst support was prepared, as described in Example 1, however, the calcination temperature was 1000° C.

Example 9

Inventive

A modified catalyst support was prepared, as described in Example 1, however, the calcination temperature was 1050° C.

Example 10

Inventive

A modified catalyst support was prepared, as described in Example 1, however, the calcination temperature was 1100° C.

Example 11

Inventive

A modified catalyst support was prepared, as described in Example 1, however, the calcination temperature was 1150° C.

Example 12

Inventive

A modified catalyst support was prepared, as described in Example 1, however, the calcination temperature was 1200° C.

Example 13

Comparative, Si Modification

Gamma alumina Puralox SCCa-150 was modified with Si, using TEOS (tetra ethoxy silane) in ethanol. TEOS (7.2 g) was added to ethanol (50 ml) and stirred for 10 minutes at 60° C. Puralox SCCa-150 (50 g) catalyst support was added to this mixture which was then stirred for another 10 minutes at 60° C. The impregnation liquid was slowly removed by gradually decreasing the pressure from atmospheric pressure to 80 mbar(a) and maintaining it at 80 mbar(a) until dryness, while the temperature was maintained at 60° C. By means of calcination at 550° C. for 2 hours in air, the modifying component containing catalyst support material was thus converted to a calcined modified catalyst support. The resulting support contained Si (1.5 wt %) deposited onto the alumina.

Example 14

Comparative, Si Modification

A modified catalyst support was prepared, as described in Example 13, however, the calcination temperature was 1100° C.

Example 15

Conductivity Measurements

Alumina dissolves in an aqueous medium at low pH. The dissolution of alumina results in the formation of aluminium ions. As more and more alumina dissolves, the concentration of aluminium increases with time. An increase in aluminium with time was followed by monitoring the conductivity at a constant pH of 2. The pH was kept constant by automated addition of a 10% nitric acid solution. The results are given in FIG. 1.

FIG. 1 shows the cumulative Al-dissolution as a function of time for Ti (Example 1 and Example 10), Si (Example 13) modified catalyst support and the un-modified support. It can be seen that the Al-dissolution for the Si-modified support and the un-modified support was faster compared to the Ti-modified supports. Furthermore, an increase in the calcination temperature for the Ti-modified support from 550° C. to 1100° C. resulted in a further decrease in the Al-dissolution rate of the support.

Example 16

Leaching Measurements

Figure 2:
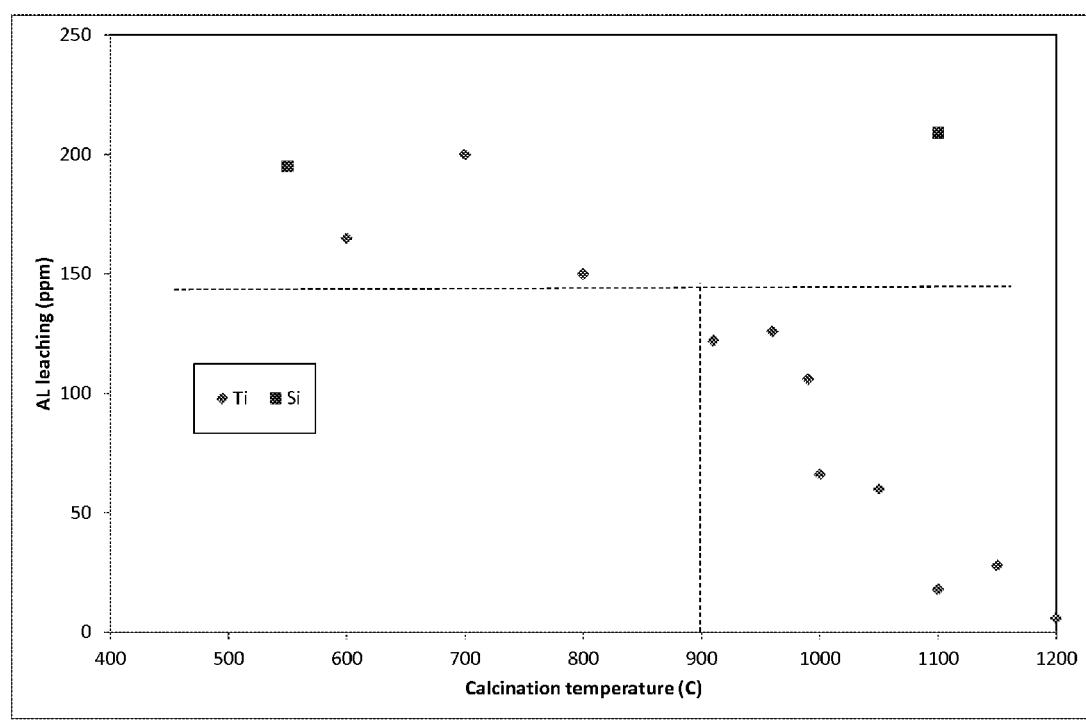
FIG. 2 shows Al-leaching over the Ti-modified and Si-modified materials as a function of calcination temperature.

Al-leaching from the supports was investigated by pumping a dilute acid solution (1% formic acid solution) over a fixed bed reactor containing the support at 60° C. and atmospheric pressure. The solution was circulated over the bed at pH=2. This continued for 30 minutes and during this period the resulting drainings were collected. Aluminium content of the solution was determined by ICP (Inductive Coupled Plasma) analysis (see Table 1 and FIG. 2).

A marked decrease in Al-leaching of the Ti-modified supports was observed with an increase in calcination temperatures. Furthermore, a significant decrease in the Al-leaching was observed for the Ti-modified supports at calcination temperatures above 900° C., clearly showing an advantage in the Al-leaching properties of the supports with calcination at these temperatures. Suppression of the solubility of the catalyst support material in aqueous acid solutions and/or neutral aqueous solutions further lowers the concentration of undesired catalyst particles, either as cobalt and/or Al, in the wax. The significant decrease in the Al-leaching with an increase in calcination temperature from 550° C. (Example 13) to 1100° C. (Example 14) was not observed for the Si-modified alumina support material (see Table 1 and FIG. 2).

TABLE 1

Al-leaching of modified catalyst support material as a function of calcination temperature.

| | Calcination, ° C. | Al-leaching$^a$, ppm | Pore volume (ml/g) |
|---|---|---|---|
| Ex 2 (comparative) | 600 | 165 | 0.44 |
| Ex 3 (comparative) | 700 | 200 | 0.44 |

TABLE 1-continued

Al-leaching of modified catalyst support material as a function of calcination temperature.

| | Calcination, ° C. | Al-leaching[a], ppm | Pore volume (ml/g) |
|---|---|---|---|
| Ex 4 (comparative) | 800 | 150 | 0.44 |
| Ex 5 (inventive) | 910 | 97 | 0.44 |
| Ex 6 (inventive) | 960 | 126 | 0.42 |
| Ex 7 (inventive) | 990 | 106 | 0.41 |
| Ex 8 (inventive) | 1000 | 66 | 0.40 |
| Ex 9 (inventive) | 1050 | 60 | 0.30 |
| Ex 10 (inventive) | 1100 | 18 | 0.28 |
| Ex 11 (inventive) | 1150 | 28 | 0.02 |
| Ex 12 (inventive) | 1200 | 6 | 0.02 |
| Ex 13 (comparative, Si) | 550 | 195 | |
| Ex 14 (comparative, Si) | 1100 | 209 | |

[a]Error = ±10 ppm

Example 17

Comparative

A modified catalyst support was prepared as described in Example 1, but the calcination was carried out at 1100° C. and sufficient $Ti(OC_2H_5)_4$ was used so that the resulting modified catalyst support contained 1 wt % Ti.

Example 18

Inventive

A modified catalyst support was prepared as described in Example 1, but the calcination was carried out at 1100° C. and sufficient $Ti(OC_2H_5)_4$ was used so that the resulting modified catalyst support contained 1.5 wt % Ti.

Example 19

Inventive

A modified catalyst support was prepared as described in Example 1, but the calcination was carried out at 1100° C. and sufficient $Ti(OC_2H_5)_4$ was used so that the resulting modified catalyst support contained 2.0 wt % Ti.

Example 20

Inventive

A modified catalyst support was prepared as described in Example 1, but the calcination was carried out at 1100° C. and sufficient $Ti(OC_2H_5)_4$ was used so that the resulting modified catalyst support contained 2.9 wt % Ti.

Example 21

Inventive

A modified catalyst support was prepared as described in Example 1, but the calcination was carried out at 1100° C. and sufficient $Ti(OC_2H_5)_4$ was used so that the resulting modified catalyst support contained 3.0 wt % Ti.

Example 22

Inventive

A modified catalyst support was prepared as described in Example 1, but the calcination was carried out at 1100° C. and sufficient $Ti(OC_2H_5)_4$ was used so that the resulting modified catalyst support contained 3.1 wt % Ti.

Example 23

Inventive

A modified catalyst support was prepared as described in Example 1, but the calcination was carried out at 1100° C. and sufficient $Ti(OC_2H_5)_4$ was used so that the resulting modified catalyst support contained 3.2 wt % Ti.

Example 24

Inventive

A modified catalyst support was prepared as described in Example 1, but the calcination was carried out at 1100° C. and sufficient $Ti(OC_2H_5)_4$ was used so that the resulting modified catalyst support contained 3.3 wt % Ti.

Example 25

Inventive

A modified catalyst support was prepared as described in Example 1, but the calcination was carried out at 1100° C. and sufficient $Ti(OC_2H_5)_4$ was used so that the resulting modified catalyst support contained 3.4 wt % Ti.

Example 26

Comparative

A modified catalyst support was prepared as described in Example 1, but the calcination was carried out at 1100° C. and sufficient $Ti(OC_2H_5)_4$ was used so that the resulting catalyst support contained 3.5 wt % Ti.

Example 27

Comparative

A modified catalyst support was prepared as described in Example 1, but the calcination was carried out at 1100° C. and sufficient $Ti(OC_2H_5)_4$ was used so that the resulting catalyst support material contained 5 wt % Ti.

Example 28

Delta $D_{10}$

The Delta $D_{10}$ attrition index, a single impact test, was utilized to investigate the physical strength of the silica modified supports. The Delta $D_{10}$ attrition index is determined by using the Malvern Digisizer 2000. During analysis, particles are impinged onto a steel plate and the amount of breakage gives an indication of the physical strength of the particles. ±2.5 g of sample is used for an analysis. To determine the Delta $D_{10}$ value, two measurements are required, one at an air pressure setting of 0.15 bar and one at an air pressure setting of 3.0 bar. The Delta $D_{10}$ attrition index value is calculated by subtracting the Delta $D_{10}$ value at an air pressure of 3.0 bar from the Delta $D_{10}$ value at an air pressure of 0.15 bar (see results within Table 2). The Delta $D_{10}$ attrition index is an indication of the attrition resistance, thus the lower the value, the better is the attrition resistance.

TABLE 2

The Al-leaching and Delta $D_{10}$ values for Ti-modified alumina supports calcined at 1100° C. at different Ti loadings.

| | Ti, wt % | Al-leaching[a], ppm | Delta $D_{10}$[b] |
|---|---|---|---|
| Ex 17 (comparative) | 1 | 166 | 3.0 |
| Ex 18 (inventive) | 1.5 | 56 | 3.1 |
| Ex 19 (inventive) | 2.0 | 18 | 5.6 |
| Ex 10 (inventive) | 2.6 | 18 | 5.9 |
| Ex 20 (inventive) | 2.9 | 15 | 5.4 |
| Ex 21 (inventive) | 3.0 | 9 | 6.8 |
| Ex 22 (inventive) | 3.1 | 2 | 6.7 |
| Ex 23 (inventive) | 3.2 | 15 | 6.3 |
| Ex 24 (inventive) | 3.3 | 6 | 6.6 |
| Ex 25 (inventive) | 3.4 | 6 | 7.0 |
| Ex 26 (comparative) | 3.5 | 18 | 10.3 |
| Ex 27 (comparative) | 5 | 16 | 9.6 |

[a]Error ±10 ppm
[b]Error ±1 unit

An increase in the Ti loading above 1 wt % resulted in a significant decrease in the Al-leaching. However, with an increase in the Ti content to or above 3.5 wt % the $D_{10}$ (mechanical strength) of the support decreased, indicating lower attrition resistance.

Example 29

Inventive

A modified catalyst support was prepared as described in Example 1, except that the titanium source was titanium(iv) butoxide and the calcination was carried out at 1100° C. Sufficient titanium(iv) butoxide was used so that the resulting modified catalyst support contained 2.6 wt % Ti.

Example 30

Inventive

A modified catalyst support was prepared as described in Example 1, except that the titanium source was titanium(iv) iso-propoxide and the calcination was carried out at 1100° C. Sufficient titanium(iv) iso-propoxide was used so that the resulting modified catalyst support contained 2.6 wt % Ti.

Example 31

Leaching Measurements

Leaching experiments were carried out in accordance with Example 16, using the samples from Examples 29, 30, and compared to that of Example 10 (see Table 3).

TABLE 3

Al-leaching of modified catalyst supports, prepared by means of different titanium sources.

| | Ti source | Al-leaching[a], ppm |
|---|---|---|
| Ex 10 (inventive) | Ti(OC$_2$H$_5$)$_4$ | 18 |
| Ex 29 (inventive) | Ti(IV) butoxide | 28 |
| Ex 30 (inventive) | Ti(IV) iso-propoxide | 16 |

[a]Error = ±10 ppm

Example 32

Inventive

A cobalt based Fischer-Tropsch synthesis catalyst precursor with the composition 30 gCo/0.075 gPt/100 g support was prepared from a modified catalyst support. The modified catalyst support was prepared as described in Example 1, containing Ti (2.6 wt %), except that it was calcined at 1000° C. as described in Example 8.

Example 33

Comparative

A cobalt based Fischer-Tropsch synthesis catalyst precursor was prepared in the same manner as in Example 32, however, the comparative Si-modified catalyst support of Example 13 was employed as support.

Example 34

Fischer-Tropsch Synthesis

The cobalt catalyst precursors of Examples 32 and 33 were reduced in hydrogen prior to Fischer-Tropsch synthesis in a tubular reactor at atmospheric pressure. The reduction temperature was increased to 425° C. at 1° C./min, after which isothermal conditions were maintained for 16 hours.

Between 10 g and 30 g of the resultant reduced catalyst, with catalyst particle sizes ranging between 38 μm to 150 μm, was suspended in 300 ml molten wax and loaded in a CSTR with an internal volume of 500 ml, under a nitrogen blanket.

The pressure was increased to 18 bar and the temperature to 230° C., whereafter synthesis feed gas was introduced into the CSTR. The synthesis feed gas consisted of hydrogen, carbon monoxide and 10% argon as an internal standard. This reactor was electrically heated and sufficiently high stirrer speeds were employed so as to eliminate any gas-liquid mass transfer limitations. The % $H_2$+CO conversion were maintained at 60%±2, by controlling the feed flow by means of Brooks mass flow controllers. The results are set out in Table 4.

From Table 4 it can be seen that the relative Fischer-Tropsch reaction rates and the $CH_4$ selectivities of the catalyst containing the Ti-modified catalyst support (Example 32) are comparable to those of the catalyst containing the Si-modified catalyst support (Example 33). Changing from the Si-modified catalyst support to Ti-modified catalyst support did not negatively influence FT performance of the catalyst. However, the $C_5$+ selectivity of the catalyst containing the Ti-modified catalyst support increased compared to that of the catalyst containing the Si-modified catalyst support material; thus the presence of the Ti-modified catalyst support (Example 8) enhanced the formation of the long chain hydrocarbons in the $C_5+$ selectivity. In general, the Examples have thus shown that a Ti-modified catalyst support calcined at temperatures above 900° C. resulted in a significant decrease in the Al-leaching of the modified support material without negatively affecting the FT performance. The Ti-containing catalyst support resulted in enhanced the $C_5+$ selectivity (Example 32) compared to the catalyst containing Si-modified catalyst support (Example 33).

TABLE 4

FT performance over Examples 32 and 33 after 18 days on-line.

| TOS, days | Relative FT rate[1] | $CH_4$ selectivity, C %[2] | $C_5+$ selectivity, mass %[3] |
|---|---|---|---|
| Ex 32 (inventive, Ti-modified support, calcined at 1000° C.) | | | |
| 18 | 1.0 | 5.8 | 87 |
| 32 | 0.9 | 5.6 | 88 |
| Ex 33 (comparative, Si-modified support, calcined at 550° C.) | | | |
| 18 | 0.9 | 6.0 | 85 |
| 32 | 0.8 | 6.2 | 85 |

[1]Relative to the FT rate ((CO + $CO_2$) μmol/CO/gs)) for Ex 32 after 18 days on-line and Error is 5%, e.g. 1.0 +/− 0.05
[2]C % excluding $CO_2$ formation and Error is 0.3 percentage points, e.g. 5.8 +/− 0.3
[3]Error is 1 percentage point, e.g. 87 +/− 1

Example 35

Leaching Measurements

Leaching experiments were carried out in accordance with Example 16, using a sample from Example 32, and compared to that of Example 33 (see Table 5).

TABLE 5

Al-leaching of cobalt catalysts on modified catalyst support materials.

| | Support | Al-leaching[a], ppm |
|---|---|---|
| Ex 32 (inventive) | $Ti/Al_2O_3$ | 7 |
| Ex 33 (comparative) | $Si/Al_2O_3$ | 58 |

[a]Error = ±10 ppm

Example 36

Inventive

Boehmite (150 g) was added to 200 ml of EtOH (ethanol). A solution containing 100 ml of EtOH and 25.4 g of titanium(IV) butoxide was added slowly to the boehmite-ethanol mixture. Thereafter the solvent was removed under vacuum at 80° C. and 280 mbar to give a titanium-containing catalyst support material in the form of a free flowing powder. The latter was added to 790 g of water at 90° C. and stirred with an overhead stirrer for 1.5 hours. The resultant slurry was calcined in a muffle oven at 950° C., to obtain a modified catalyst support. The Ti content of the sample was 2.2 wt %.

Example 37

Inventive

Example 37 was prepared via co-hydrolysis. For that a mixture of Al-hexanolate and titanium (IV) isopropoxide was hydrolysed by slowly adding it into water. After complete hydrolysis to obtain a titanium-containing alumina-catalyst support material, the organic phase was decanted and substituted by the same amount of water. The remaining isopropanol was removed by azeotropic water/alcohol distillation. The resulting alumina-titania slurry was aged hydrothermally at 150° C. and spray dried subsequently, to obtain a titanium-containing catalyst support material. Calcination of the titanium-containing catalyst support material was done at 950° C. A titanium level of 2.8 wt % in the resultant modified catalyst support was obtained.

Example 38

Conductivity Measurements

Figure 3:
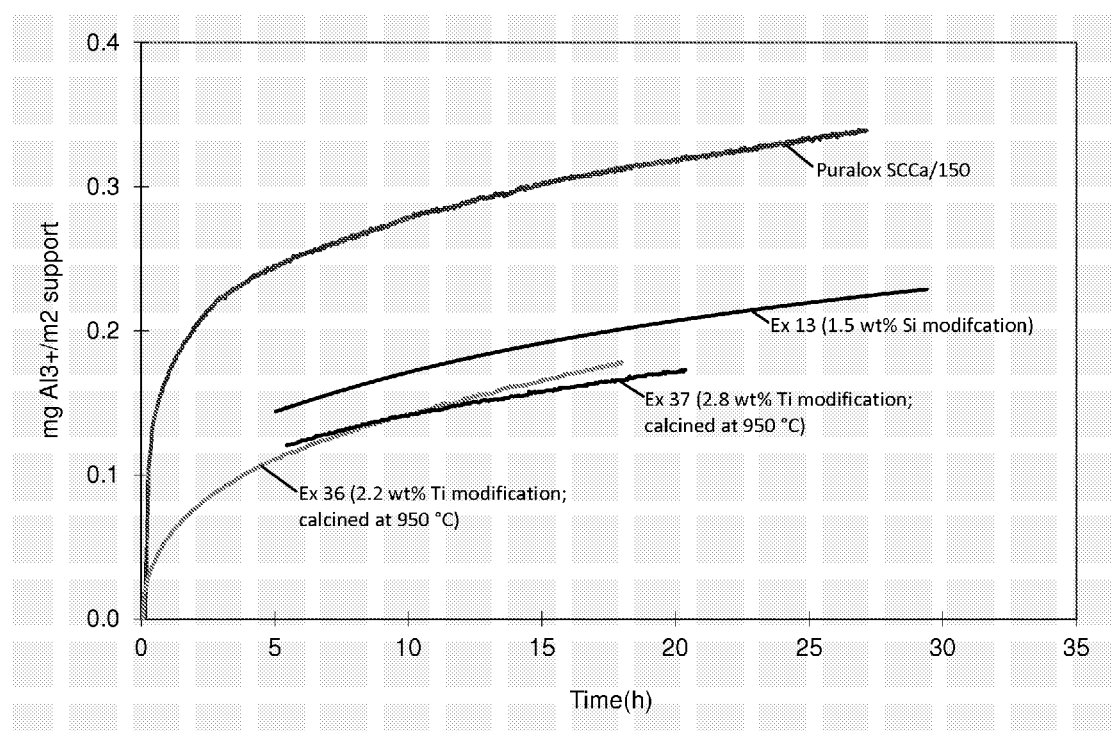
FIG. 3 shows cumulative Al dissolution as a function of time for a Ti-modified catalyst support (Example 36, Example 37), Si-modified catalyst support (Example 13) and unmodified alumina support (Puralox SCCa-/150).

Conductivity measurements were executed in the same way as in Example 15. Samples from Examples 36 and 37 were analyzed, and the results are shown in FIG. 3. These results show a strong improvement in the leaching behavior for Ti modified supports.

The invention claimed is:

1. A method of preparing a catalyst precursor, the method comprising
preparing a titanium-containing catalyst support material by
(i) contacting a catalyst support material with an organic titanium compound, wherein the catalyst support material is selected from the group consisting of (a) a catalyst support precursor comprising an aluminium compound which, upon calcination, converts to a catalyst support in the form of one or more aluminium oxides, and (b) a catalyst support being alumina in the form of one or more aluminium oxides, or
(ii) co-hydrolysing a hydrolysable organic titanium compound and Al(OR")$_3$ to form the titanium-containing catalyst support material which includes Al, wherein all R" are the same or different and are each an organic group;
calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds;
introducing a precursor compound of cobalt (Co) onto and/or into the modified catalyst support thereby to obtain a catalyst precursor; and
introducing a dopant capable of enhancing the reducibility of the cobalt (Co) onto and/or into the modified catalyst support, the dopant being introduced as a dopant compound which is a compound of a metal selected from the group consisting of palladium (Pd), platinum (Pt), ruthenium (Ru), rhenium (Re) and a mixture of two or more thereof.

2. The method according to claim 1, wherein the Ti wt % in the modified catalyst support is more than 1 and less than 3.0.

3. The method according to claim 1, wherein the preparation of the titanium-containing catalyst support material is by means of the contacting of the catalyst support material with the organic titanium compound, with the catalyst support material being the catalyst support precursor comprising the aluminium compound, and which includes shaping the catalyst support precursor into particulate form before calcination thereof.

4. The method according to claim 3, wherein the organic titanium compound is a titanium compound having only organic groups associated with the titanium thereof, with all of the organic groups being associated with the titanium by means of an oxygen atom.

5. The method according to claim 4, wherein the organic titanium compound is selected from the group consisting of titanium (IV) methoxide; titanium (IV) ethoxide; titanium (IV) propoxide; titanium (IV) isopropoxide; titanium (IV) diisopropoxide bis(acetylacetonate); titanium (IV) 2-ethylhexoxide; titanium (IV) hexoxide; titanium(IV) butoxide and titanium (IV) bis(ammonium lactato) dihydroxide.

6. The method according to claim 1, wherein the preparation of the titanium-containing catalyst support material is by the co-hydrolysis of the hydrolysable organic titanium compound and the $Al(OR'')_3$, with the co-hydrolysis of the hydrolysable organic titanium compound and the $Al(OR'')_3$ being carried out by mixing the hydrolysable organic titanium compound and the $Al(OR'')_3$ and hydrolysing the resultant mixture.

7. The method according to claim 6, wherein the titanium-containing catalyst support material is titanium-containing boehmite.

8. The method according to claim 6, wherein the hydrolysable organic titanium compound is a titanium compound wherein all the groups associated with the titanium are organic groups, with all of the organic groups being associated with the titanium by means of an oxygen atom.

9. The method according to claim 8, wherein the hydrolysable organic titanium compound is selected from the group consisting of titanium (IV) methoxide; titanium (IV) ethoxide; titanium (IV) propoxide; titanium (IV) isopropoxide; titanium (IV) diisopropoxide bis(acetylacetonate); titanium (IV) 2-ethylhexoxide; titanium (IV) hexoxide; titanium(IV) butoxide and titanium (IV) bis(ammonium lactato) dihydroxide.

10. The method according to claim 6, wherein R'' of $Al(OR'')_3$ is an acyl or hydrocarbyl group or is a heterohydrocarbyl group.

11. The method according to claim 1, wherein the calcination of the titanium-containing support material is carried out at a temperature of at least 960° C., but below 1150° C.

12. A method of preparing a catalyst, which includes
preparing a titanium-containing catalyst support material by
(i) contacting a catalyst support material with an organic titanium compound, wherein the catalyst support material is selected from the group consisting of (a) a catalyst support precursor comprising an aluminium compound which, upon calcination, converts to a catalyst support in the form of one or more aluminium oxides, and (b) a catalyst support being alumina in the form of one or more aluminium oxides, or
(ii) co-hydrolysing a hydrolysable organic titanium compound and $Al(OR'')_3$ to form the titanium-containing catalyst support material which includes Al,
wherein all R'' are the same or different and are each an organic group;
calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds;
introducing a precursor compound of cobalt (Co) onto and/or into the modified catalyst support thereby to obtain a catalyst precursor;
introducing a dopant capable of enhancing the reducibility of the cobalt (Co) onto and/or into the modified catalyst support, the dopant being introduced as a dopant compound which is a compound of a metal selected from the group consisting of palladium (Pd), platinum (Pt), ruthenium (Ru), rhenium (Re) and a mixture of two or more thereof; and
reducing the said catalyst precursor, thereby activating the catalyst precursor and obtaining the catalyst.

13. A hydrocarbon synthesis process which comprises
preparing a titanium-containing catalyst support material by
(i) contacting a catalyst support material with an organic titanium compound, wherein the catalyst support material is selected from the group consisting of (a) a catalyst support precursor comprising an aluminium compound which, upon calcination, converts to a catalyst support in the form of one or more aluminium oxides, and (b) a catalyst support being alumina in the form of one or more aluminium oxides, or
(ii) co-hydrolysing a hydrolysable organic titanium compound and $Al(OR'')_3$ to form the titanium-containing catalyst support material which includes Al,
wherein all R'' are the same or different and are each an organic group;
calcining the titanium-containing catalyst support material at a temperature above 900° C. to obtain a modified catalyst support which includes more than 1 wt % and less than 3.5 wt % Ti, based on the weight of the modified catalyst support, the Ti being present in the form of one or more titanium compounds;
introducing a precursor compound of cobalt (Co) onto and/or into the modified catalyst support thereby to obtain a catalyst precursor;
introducing a dopant capable of enhancing the reducibility of the cobalt (Co) onto and/or into the modified catalyst support, the dopant being introduced as a dopant compound which is a compound of a metal selected from the group consisting of palladium (Pd), platinum (Pt), ruthenium (Ru), rhenium (Re) and a mixture of two or more thereof;
reducing the said catalyst precursor, thereby activating the catalyst precursor and obtaining the catalyst; and
contacting hydrogen with carbon monoxide at a temperature above 100° C. and a pressure of at least 10 bar with the catalyst, to produce hydrocarbons and, optionally, oxygenates of hydrocarbons.

* * * * *